United States Patent [19]

Hilse

[11] Patent Number: 4,591,355
[45] Date of Patent: May 27, 1986

[54] CLOSE CLEARANCE SEAL FOR ROTATABLE THERAPEUTIC CATHETERS

[75] Inventor: Gernot R. K. Hilse, Woodinville, Wash.

[73] Assignee: Advanced Technology Laboratories, Inc., Bothell, Wash.

[21] Appl. No.: 625,074

[22] Filed: Jun. 27, 1984

[51] Int. Cl.[4] .............................................. A61M 5/18
[52] U.S. Cl. .................................... 604/159; 128/305
[58] Field of Search ................ 604/156, 159, 264, 22, 604/280, 283; 128/305, 751

[56] References Cited

U.S. PATENT DOCUMENTS

| | | | | |
|---|---|---|---|---|
| 3,844,272 | 10/1974 | Banko | ............................... | 604/22 X |
| 3,906,954 | 9/1975 | Baehr et al. | ........................ | 128/305 |
| 4,159,022 | 6/1979 | Pevsner | ................................. | 604/159 |
| 4,167,944 | 9/1979 | Banko | ................................. | 128/305 |

Primary Examiner—John D. Yasko
Attorney, Agent, or Firm—Lawrence S. Levinson; Sanford J. Asman

[57] ABSTRACT

The present invention relates to a seal for a rotatable therapeutic catheter, such as a motor driven therapeutic catheter. The seal is made of a drive shaft which extends through an elongated bushing. The combined drive shaft and bushing form a low-friction axle/bearing combination such that there is little friction between them. In addition, the long restrictive path between the drive shaft and the bushing serves to prevent leakage between them.

9 Claims, 3 Drawing Figures

CLOSE CLEARANCE SEAL FOR ROTATABLE THERAPEUTIC CATHETERS

BACKGROUND OF THE INVENTION

The present invention relates to a seal of the type used in surgical applications. In particular, the seal of the present invention is intended for use with therapeutic catheters which utilize a driven shaft to rotate a tool within a patient's body.

In the past, physicians performing arteriography/venography on patients were restricted to simple documentation of vascular condition. Through the use of injectable X-ray contrast material, they could generate and record X-ray images of the affected vessel, duct, or organ. Such X-ray images could be used by the physician and a surgeon to determine appropriate treatment.

Currently, physicians are actually treating patients percutaneously, using such devices as guide catheters, steerable guide wires, balloon dilatation devices, aortic balloon pumps, and vena caval filters. In most of these procedures, a guide wire is inserted into and threaded through the vessel lumen until the distal tip is at or past the site of treatment. A guide catheter (or sheath), usually preformed, is then slipped over the guide wire and advanced to a location which is just proximal to the site of treatment. Finally, the therapeutic catheter, e.g., a balloon dilatation catheter, is inserted over the guide wire and advanced to the site within the vessel lumen. Since the guide catheter and therapeutic catheter often have their distal tips located at points with high perfusion pressure (e.g., 200 mm Hg for a hypertensive patient), there is a strong tendency for blood to flow in the clearance space between the therapeutic catheter and the guide catheter. To prevent this from occurring, it is common to use a hemostasis seal, often in the form of an O-ring or rubber septum. These seals are often fitted with Luer lock fittings to permit injection of contrast solution or drugs or to permit the extraction of fluids.

In U.S. Pat. No. 4,445,509 entitled METHOD AND APPARATUS FOR REMOVAL OF ENCLOSED ABNORMAL DEPOSITS which issued on May 1, 1984 to David C. Auth a therapeutic catheter device is described which would enable the removal of deposits from the interior wall of a patient's vessel. As more fully described in that patent, which is incorporated herein by reference, a differential cutting tool on the end of a flexible drive shaft is inserted into the affected vessel, and the drive shaft is rotated at high speed to cause the cutting tool to remove the abnormal deposits from the vessel wall.

In such catheterization systems, in which the therapeutic catheter must rotate at high speed within the guide catheter, the conventional hemostasis seal used between catheters and guide wires will not work, because the conventional resilient contact between the O-ring seal and the therapeutic catheter would lead to frictional heating and eventual destruction of the seal. Accordingly, an improved seal for use with motor driven therapeutic catheters would be desirable.

SUMMARY OF THE INVENTION

To avoid the problem of seal breakdown when motor driven therapeutic catheter devices are used, the present invention uses a seal having extremely close clearance to prevent migration of body fluids between the catheters, and to allow injection at high pressure or extraction at high vacuum.

The close tolerance seal of the present invention is comprised of a precision ground shaft which has been finished to a very closely controlled dimension on its outside diameter and a bushing which is precision and finish machined to a very closely controlled dimension on its inside diameter.

DETAILED DESCRIPTION OF THE PREFERRED EMBODIMENT

Figure 1:
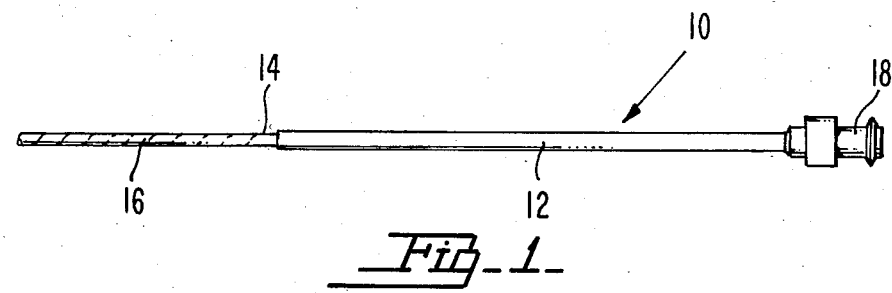
FIG. 1 is a side view showing a drive shaft of the type used in the present invention.

Referring generally to FIG. 1, the therapeutic catheter drive shaft 10 of the preferred embodiment of the invention is shown. The therapeutic drive shaft 10 is comprised of a cylindrical portion 12 which is machined to have a very precise outside diameter. In the preferred embodiment of the invention, the cylindrical portion 12 of the drive shaft 10 is comprised of No. 303 stainless steel having an outside diameter of 124.75 mils and a length of approximately 3 inches. The cylindrical portion 12 of the drive shaft 10 is attached at one end 14 to a flexible therapeutic catheter 16 which may be of the type described by Auth in the patent identified above. A drive hub 18 is attached to the other end of the cylindrical portion 12 of the drive shaft 10. The drive hub is used to turn the shaft 10 when the shaft 10 is within the guide catheter seal 20 shown in FIG. 2.

Figure 2:
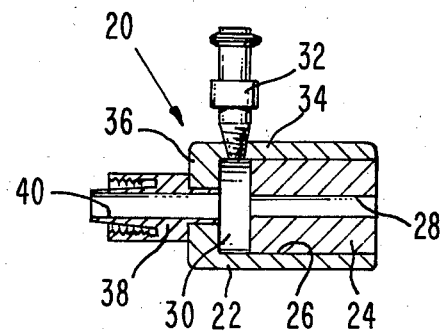
FIG. 2 is a cross-sectional view of the bushing used in the present invention.

With reference to FIG. 2, the guide catheter seal 20 is comprised of a substantially cylindrical body 22 having a bronze bushing 24 inserted within a cylindrical opening 26 formed within the body 22. The bronze bushing 24 is preferably machined to have a cylindrical inside diameter opening 28 having a very accurate inside diameter approximately 0.2 mils greater than the outside diameter of the cylindrical portion 12 of the drive shaft 10. The bronze bushing 24 has a length which is somewhat less than the length of the cylindrical opening 26 within the body 22 in order to thereby form a cavity 30 with the guide catheter seal 20.

In the preferred embodiment of the invention, a side port Luer lock fitting 32 is attached through a side wall 34 of the body 22 to connect lumen of the side port Luer fitting 32 with the cavity 30. Also connected to the cavity 30, through a front wall 36 of the catheter seal 20, is a male Luer lock fitting 38. The male Luer lock fitting 38 has an internal opening 40 which is connected through the front wall 36 to the cavity 30.

Figure 3:
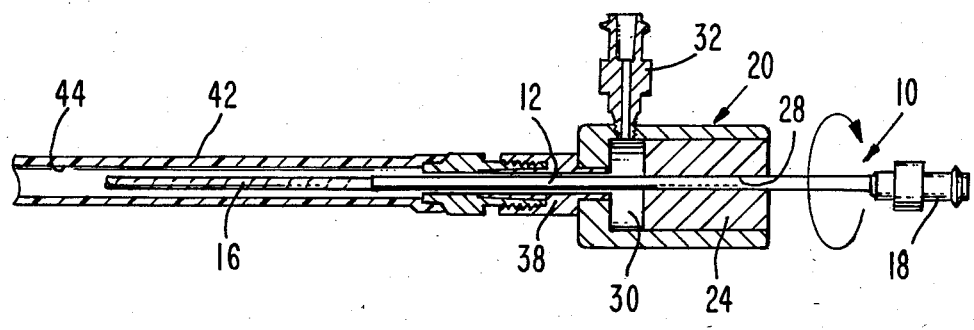
FIG. 3 is a side view of the guide catheter seal assembly including the drive shaft of FIG. 1 and the bushing of FIG. 2.

Referring now to FIG. 3, when the drive shaft 10 is assembled with the guide catheter seal 20, and the guide catheter seal 20 is attached to a guide catheter 42 via the male Luer fitting 38, a passage 44 for fluids exists around the therapeutic catheter 16 within the guide catheter 42. Accordingly, fluids, such as medications, may be injected through the side port Luer lock fitting 32 into the internal cavity 30, and they will then travel along the cylindrical portion 12 of the drive shaft 10 through the male Luer lock fitting 38 into the passage 44 surrounding the flexible therapeutic catheter 16 and within the guide catheter 42.

Due to the close tolerance between the dimensions of the internal opening 28 in the bronze bushing 24 and the external dimensions of the cylindrical portion 12 of the drive shaft 10, an axle/bearing combination is formed. The axle/bearing combination allows for low frictional drag. However, the long, restrictive passage between the bushing 24 and the shaft 12, typically on the order of 0.75 inches in the preferred embodiment of the invention, has been found to prevent all but slight weepage at injection pressures up to about 200 pounds per square inch (psi). Similarly, when the side port Luer lock fitting 32 is used for suction, the seal between the cylindrical portion 12 of the drive shaft 10 and the cylindrical opening 28 in the bushing 24 operates to adequately prevent suction therethrough.

As will be recognized by those skilled in the art, it is quite important to the present seal that the cylindrical portion 12 of the drive shaft 10 bear closely against the cylindrical opening 28 with minimal frictional losses therebetween. Accordingly, the cylindrical portion 12 of the drive shaft 10 is smoothly finished prior to assembly. In the preferred embodiment of the invention, the cylindrical portion 12 of the drive shaft 10 was made of 303 stainless steel, and the outside diameter of the cylindrical portion 12 of the drive shaft 10 was selected to be 0.12475 +0.0000/−0.0001 inch, with a surface finish of RMS 8.

Similarly, the cylindrical opening 28 must be reamed to an accurate inside dimension. In the preferred embodiment of the invention, the the bushing 24 was made of bearing bronze, and the inside diameter of the cylindrical opening 28 was reamed to 0.1250 +0.0000/−0.0002 inch, with a surface finish of RMS 16.

I claim:

1. A close clearance fluid and gas seal for use with motor drive therapeutic catheters comprising:
    (a) a drive shaft including an elongated, cylindrical portion having motor connection means at one end, said elongated cylindrical, portion having a first outside diameter, said drive shaft further comprising a flexible catheter attached at the end remote from the end having said motor connection means; and
    (b) a bushing having a cylindrical opening formed therethrough, said cylindrical opening being formed to have an inside diameter which is substantially the same, but slightly more than, said first outside diameter.

2. The close clearance hemostatic seal of claim 1 in which said elongated, cylindrical portion of said drive shaft is comprised of stainless steel.

3. The close clearance seal of claim 2 in which said bushing is substantially cylindrical and extends into a substantially cylindrical opening in a substantially cylindrical body, said body having a substantially cylindrical opening formed therein from one end with a wall at the opposite end, said bushing extends into said substantially cylindrical opening from said open end, there being a cylindrical opening in said wall of said body which is a continuation of said cylindrical opening in said bushing.

4. The close clearance seal of claim 3 in which said bushing is shorter in the axial direction than said substantially cylindrical opening in said body, and wherein said bushing is not fully inserted into said substantially cylindrical opening, whereby a cavity is formed within said body between said front wall and said bushing.

5. The close clearance seal of claim 4 further comprising means for connecting said bushing to a guide catheter.

6. The close clearance seal of claim 5 wherein said means for connecting said bushing to a guide catheter comprises a Luer lock fitting.

7. The close clearance seal of claim 6 further comprising an opening in said wall of said body which extends into said cavity.

8. The close clearance seal of claim 7 further comprising means for connecting a fluid containing vessel to said opening to said cavity.

9. The close clearance seal of claim 8 in which said means for connecting a fluid containing vessel to said opening to said cavity comprises a Luer lock fitting.

* * * * *